(12) United States Patent
Rahimy et al.

(10) Patent No.: US 9,254,361 B2
(45) Date of Patent: Feb. 9, 2016

(54) DRIP CHAMBER FOR AN INFUSION DEVICE

(75) Inventors: Ismael Rahimy, Friedberg (DE); Torsten Brandenburger, Reichelsheim (DE)

(73) Assignee: Fresenius Kabi Deutschland GmbH, Bad Homburg V.D.H. (DE)

( * ) Notice: Subject to any disclaimer, the term of this patent is extended or adjusted under 35 U.S.C. 154(b) by 1248 days.

(21) Appl. No.: 12/312,404

(22) PCT Filed: Nov. 7, 2007

(86) PCT No.: PCT/EP2007/009618
§ 371 (c)(1),
(2), (4) Date: Aug. 20, 2009

(87) PCT Pub. No.: WO2008/058656
PCT Pub. Date: May 22, 2008

(65) Prior Publication Data
US 2010/0063456 A1     Mar. 11, 2010

(30) Foreign Application Priority Data
Nov. 11, 2006   (DE) .......................... 10 2006 053 219

(51) Int. Cl.
| | |
|---|---|
| *A61M 5/162* | (2006.01) |
| *A61M 5/168* | (2006.01) |
| *A61J 1/14* | (2006.01) |
| *A61M 5/14* | (2006.01) |
| *A61M 39/10* | (2006.01) |
| *A61J 1/10* | (2006.01) |
| *A61M 39/14* | (2006.01) |

(52) U.S. Cl.
CPC .............. *A61M 5/162* (2013.01); *A61J 1/1475* (2013.01); *A61M 5/1411* (2013.01); *A61M 39/10* (2013.01); *A61J 1/10* (2013.01); *A61M 39/14* (2013.01); *A61M 2039/1027* (2013.01)

(58) Field of Classification Search
CPC ....... A61J 1/1475; A61J 1/10; A61M 5/1411; A61M 39/10; A61M 5/162; A61M 2039/1027; A61M 39/14

USPC ......... 604/244, 246, 251, 255, 256, 533, 534, 604/535, 536, 538, 539, 403, 408, 411, 414, 604/415
See application file for complete search history.

(56) References Cited

U.S. PATENT DOCUMENTS

| 5,334,188 A | * | 8/1994 | Inoue et al. ................... 604/539 |
|---|---|---|---|
| D356,150 S | | 3/1995 | Duggan et al. |

(Continued)

FOREIGN PATENT DOCUMENTS

| DE | 197 48 497 A1 | 5/1999 |
|---|---|---|
| DE | 202 16 791 UI | 2/2003 |

(Continued)

OTHER PUBLICATIONS

International Preliminary Report on Patentability of PCT/EP2007/009618, date of mailing Jun. 18, 2009, date of issuance Jun. 10, 2009.

(Continued)

*Primary Examiner* — Theodore Stigell
(74) *Attorney, Agent, or Firm* — Hamilton, Brook, Smith & Reynolds, P.C.

(57) ABSTRACT

The application relates to a drip chamber for an infusion device, to an infusion device with a drip chamber, and to an arrangement composed of an infusion container and of such an infusion device. The drip chamber has a securing part for securing the drip chamber releasably to the infusion container. The securing part of the drip chamber has securing elements which are arranged along the circumference of a circle and which, on the inner sides facing each other, have grooves extending along the circumference of a circle. The securing elements can be spread from a position in which they engage firmly around the connector part of the infusion container to a position in which they release the connector part of the infusion device. The securing elements secure the piercing spike of the drip chamber against slipping out of the piercing part of the connector part of the infusion container.

12 Claims, 5 Drawing Sheets

(56) References Cited

U.S. PATENT DOCUMENTS

Figure 1:
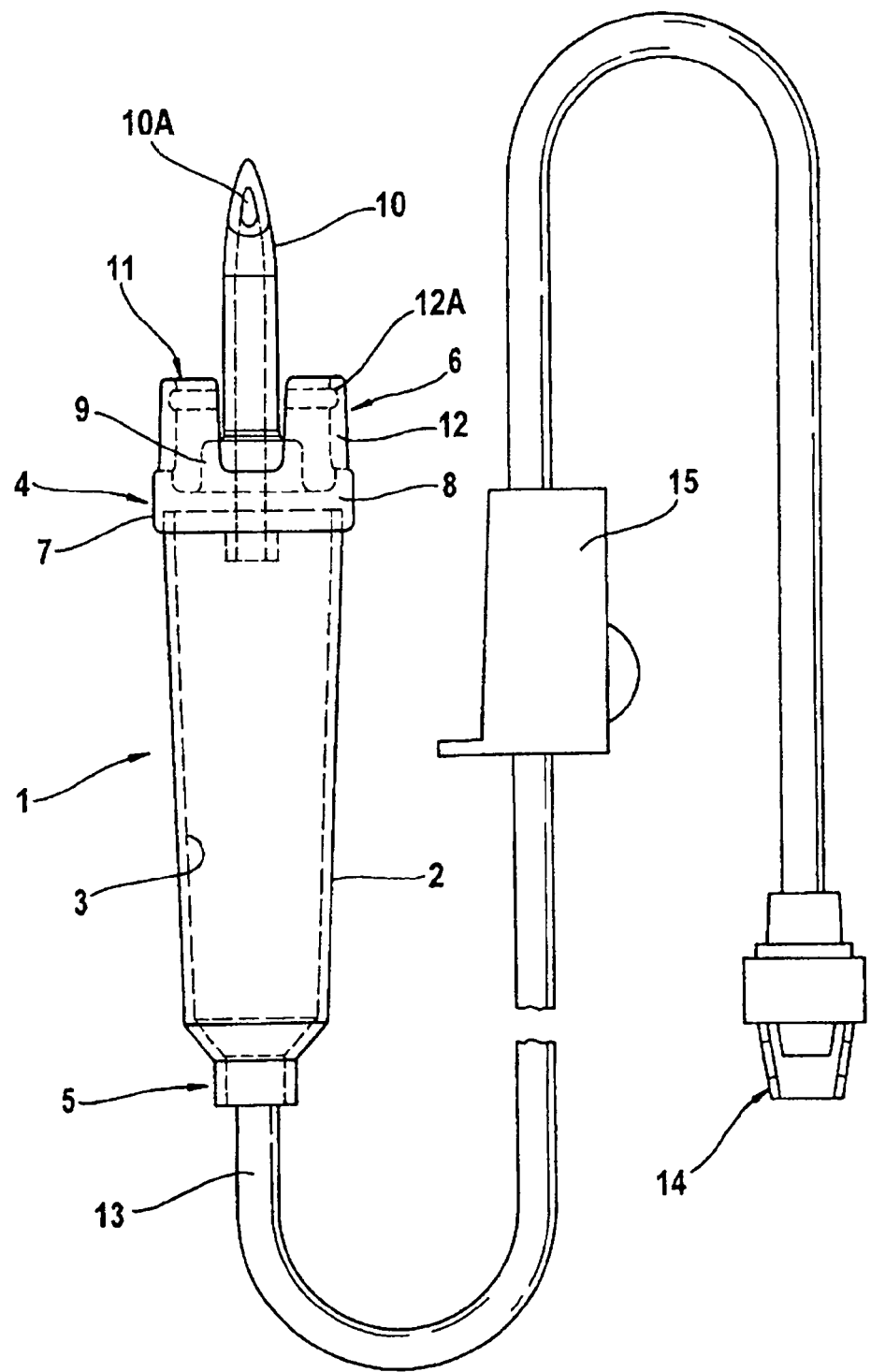

| | | | |
|---|---|---|---|
| 5,735,826 | A | 4/1998 | Richmond |
| 2004/0243065 | A1* | 12/2004 | McConnell et al. .......... 604/183 |
| 2005/0124942 | A1 | 6/2005 | Richmond |

FOREIGN PATENT DOCUMENTS

| | | | |
|---|---|---|---|
| JP | 54025194 Y2 | | 12/1975 |
| JP | Sho 50-155183 | * | 12/1975 |
| JP | Sho 50-155183 A | | 12/1975 |
| JP | 2003-47663 | * | 2/2003 |
| JP | 2003-47663 A | | 2/2003 |
| WO | WO 2005/037362 A1 | | 4/2005 |

OTHER PUBLICATIONS

International Search Report of PCT/EP2007/009618, date of mailing Mar. 10, 2008.

Notification of Reason for Refusal of Patent Application No. 2009-535615, date of mailing Jun. 19, 2012, 2 pages.

* cited by examiner

DRIP CHAMBER FOR AN INFUSION DEVICE

This application is the U.S. National Stage of International Application No. PCT/EP2007/009618, filed Nov. 7, 2007, which designates the U.S., published in German, and claims priority under 35 U.S.C. §§119 or 365(c) to German Application No. 102006053219.8, filed Nov. 11, 2006.

The invention relates to a drip chamber for an infusion device, with which medical solutions, for example infusion solutions for chemotherapy, are fed to a patient. The invention also relates to an infusion device with a drip chamber as well as an arrangement comprising an infusion container for accommodating a medical fluid and such an infusion device.

The known infusion devices comprise drip chambers which effectively prevent the entry of air into the infusion line, especially when the infusion container is being drained off.

DE 197 48 497 A1 describes an infusion device with a drip chamber and an infusion line. The drip chamber comprises an essentially cylindrical housing body with a distal inlet and a proximal outlet. A connector part for connecting the drip chamber to a connector part of an infusion container is provided at the distal inlet of the housing body. The connector part of the drip chamber comprises a piercing spike with a fluid channel which, for the purpose of connecting the drip chamber, is inserted into a piercing part of the connector part of the infusion container. Connected to the proximal outlet of the housing body is an infusion line which can be pinched off with a roller clamp. The infusion line comprises a proximal connection piece for the connection of an infusion cannula.

The known infusion devices comprising a piercing spike have the advantage that a rapid connection between the infusion container, for example an infusion bag, is possible. A drawback, however, is that there is a risk of detachment of the drip chamber from the infusion bag. Especially in the case of jerky movements made by the patient, for example when eating, drinking or walking, the piercing spike of the drip chamber can easily become detached from the piercing part of the infusion container, so that the whole system is no longer tight. The consequence is an escape of infusion solution from the infusion container. Especially when use is made of highly toxic drugs, for example cytostatics, there is a risk of contamination of the nursing staff or the patient's visitors.

U.S. Pat. No. 5,735,826 describes an arrangement comprising an infusion container, in particular an infusion bag, and an infusion device which comprises a drip chamber. The infusion bag and drip chamber each have connection pieces which enable a needle-less connection. A detachable connection is thus created without the risk of the drip chamber becoming detached from the infusion bag during the infusion. A drawback, however, is that the infusion system provides special connection pieces which do not have the piercing spikes and piercing parts tried and tested in practice.

There is known from U.S. Pat. No. 356,150 a drip chamber for an infusion device, which has a screwed connection with which the drip chamber is screwed to an infusion container, in particular an infusion bottle. Here too, it proves to be a drawback that use is not made of the tried and tested piercing spikes and piercing parts.

US 2005/0124942 A1 discloses an infusion system, wherein the drip chamber of the infusion device comprises a piercing spike, which is inserted into a piercing part of the infusion container. For the securing of the drip chamber to the infusion container, use is made of a fixing clamp, which comprises two opposite-lying hooks which are fixed to the drip chamber in a spring-loaded manner. The two hooks engage behind the connector part of the infusion container when the piercing spike is inserted into the piercing part, so that the drip chamber is secured reliably to the infusion container.

The infusion system known from US 2005/0124942 A1 ensures that the drip chamber cannot become inadvertently detached from the infusion container, but there is the drawback that lateral movements of the drip chamber are still possible with a certain amount of play, as a result of which the piercing spike is subjected to undesirable strains in the piercing part. Moreover, the handling is made difficult when the drip chamber is connected to the infusion container. For the connection of the drip chamber to the infusion container, the two hooks of the fixing clamps must be pushed radially outwards in order to be able to insert the piercing spike into the piercing part of the container.

The object underlying the invention is to make available a drip chamber for an infusion device which is easy to handle and which permits a reliable connection of infusion device and infusion container. Furthermore, it is an object of the invention to provide an infusion device with such a drip chamber that is easy to handle as well as an arrangement that is easy to handle comprising an infusion container and a drip chamber which enable a reliable connection.

In the drip chamber according to the invention, the securing part for securing the drip chamber to the infusion container comprises a plurality of, i.e. at least three, securing elements which are disposed along the circumference of a circle. At the inner sides facing each other, the securing elements comprise grooves which run along the circumference of a circle.

The securing elements are constituted in such a way that they can be spread from a position firmly engaging around the securing part of the connector part of the infusion container into a position releasing the securing part of the infusion device. The securing elements of the drip chamber according to the invention engage around the securing part of the infusion container on all sides, so that the drip chamber is held securely to the infusion container. The securing elements disposed at the circumference prevent lateral movements of the drip chamber, so that the piercing spike is not subjected to undesirable strains in the piercing part.

Whilst the securing elements of the securing part of the drip chamber comprise grooves, the securing part of the connector part of the infusion container comprises a peripheral shoulder, which is constituted such that the peripheral shoulder is secured in a snap-in manner in the grooves of the securing part of the drip chamber. The effect of this is that the drip chamber can easily be secured to the infusion container. For the snap-in securing of the drip chamber of the infusion container, it is in principle not necessary to spread the securing elements apart, since the securing elements are pushed outwards by themselves when the connector parts are joined together until the peripheral shoulder snaps into the grooves.

The connection of the drip chamber and the infusion container can be a connection which in principle is again detachable, even if the connection is constituted such that the drip chamber and infusion container cannot be detached from one another when the arrangement is used. It is however also possible to design the connection in such a way that a subsequent detachment of the connection is not possible without damage to the connector parts. For this purpose, undercuts or suchlike can for example be provided, so that the securing elements are permanently secured after the connector parts have been joined together.

In a preferred embodiment of the drip chamber, the piercing spike is disposed in the centre of the securing elements and projects beyond the securing elements. The effect of this is that the piercing spike of the drip chamber first pierces the piercing part of the infusion container, before the connector parts of drip chamber and infusion container are connected to one another.

For production-related reasons, a further preferred embodiment of the drip chamber makes provision such that its securing part is constituted as cap-shaped body which is placed onto the housing body of the drip chamber. The housing body of the drip chamber and the securing part can thus be produced in separate process steps. In principle, however, it is also possible to design the housing body of the drip chamber and the securing part in one piece.

In a further, particularly preferred embodiment, the cap-shaped body of the securing part of the drip chamber comprises a cylindrical base part placed onto the housing body of the drip chamber, on which base part the securing elements are formed.

The base part of the securing part of the drip chamber preferably comprises a central mounting piece which surrounds the piercing spike. The piercing spike is preferably a one-piece component of the mounting piece, but the piercing spike can also be inserted into the mounting piece and connected, for example welded or glued, to the latter.

For production-related reasons, the connector part of the drip chamber is preferably an injection-moulded part, which can be produced cost-effectively in large-scale manufacture.

The infusion device according to the invention comprises the drip chamber according to the invention and an infusion line which is to be connected to a patient and which is connected to the proximal outlet of the housing body of the drip chamber.

The invention is explained in greater detail below by reference to the drawings.

Figure 2:
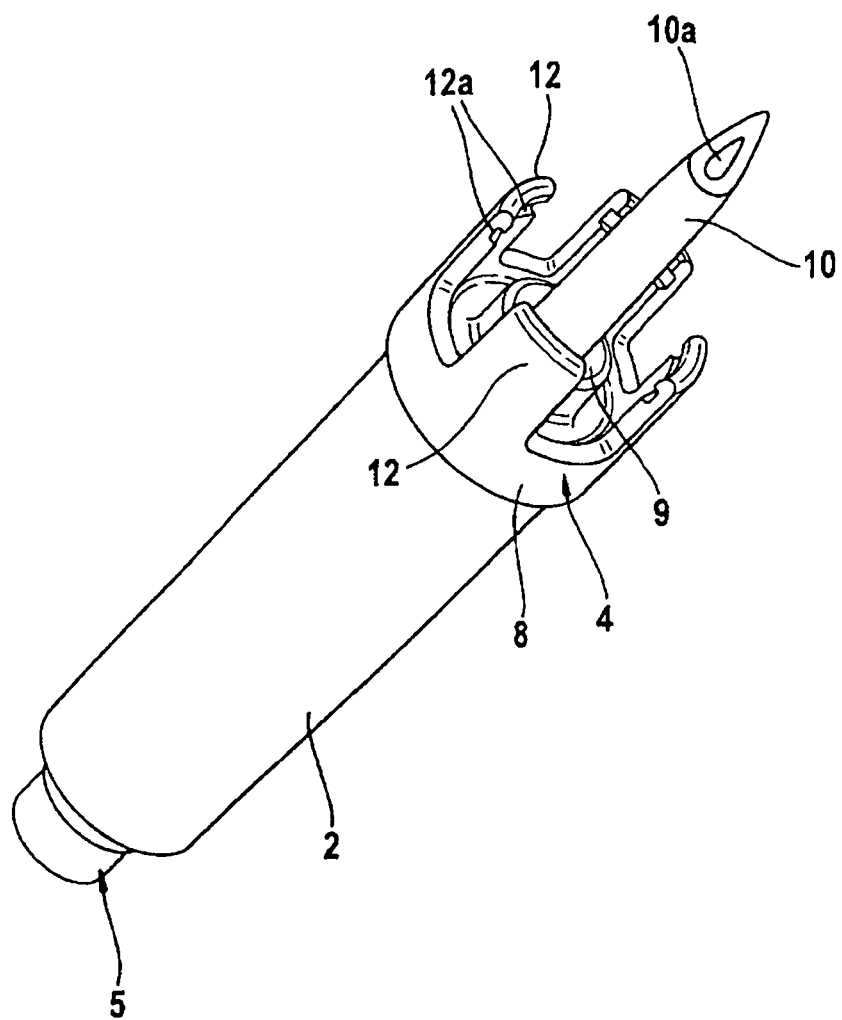
Figure 3:
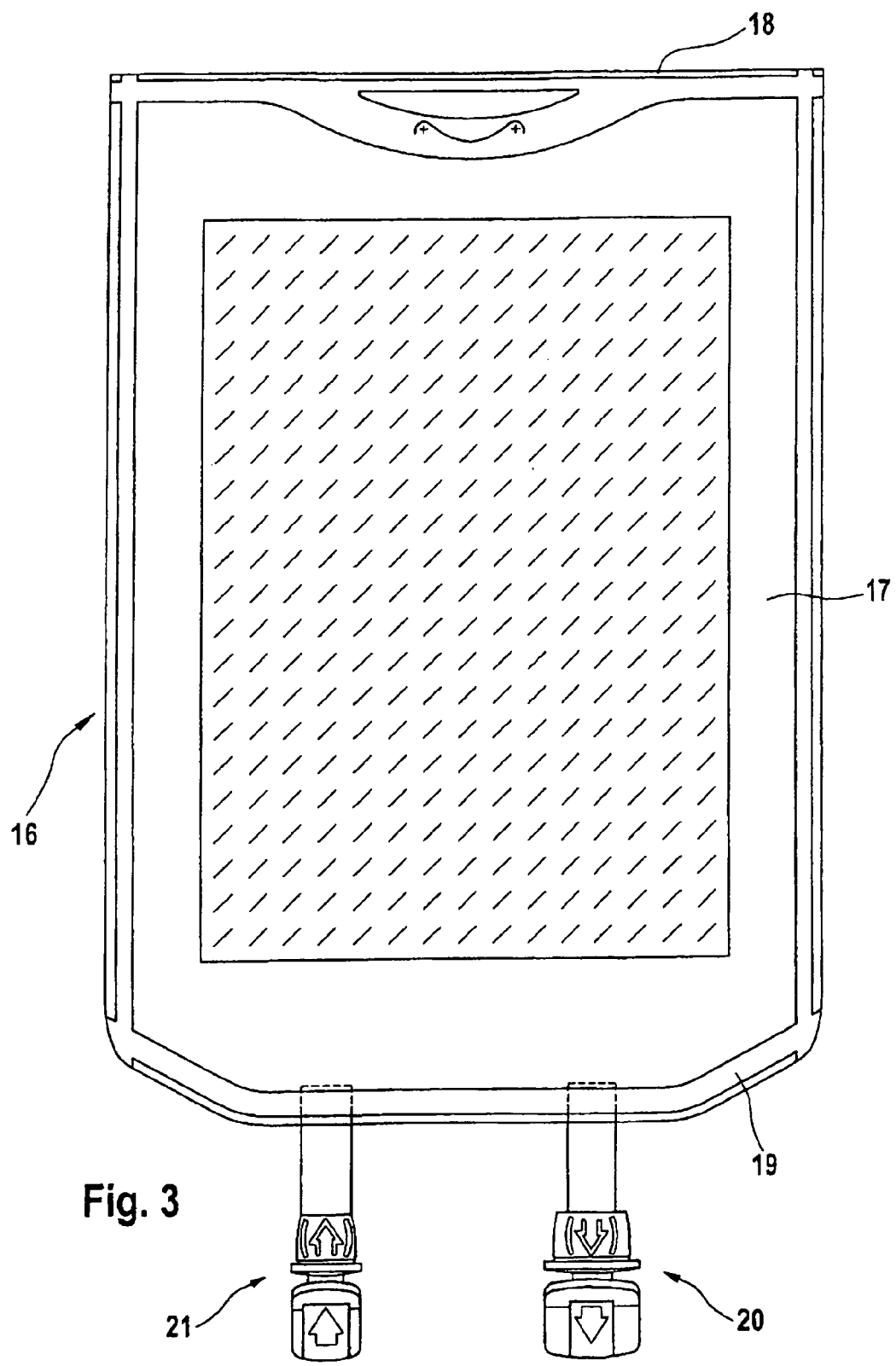
Figure 4:
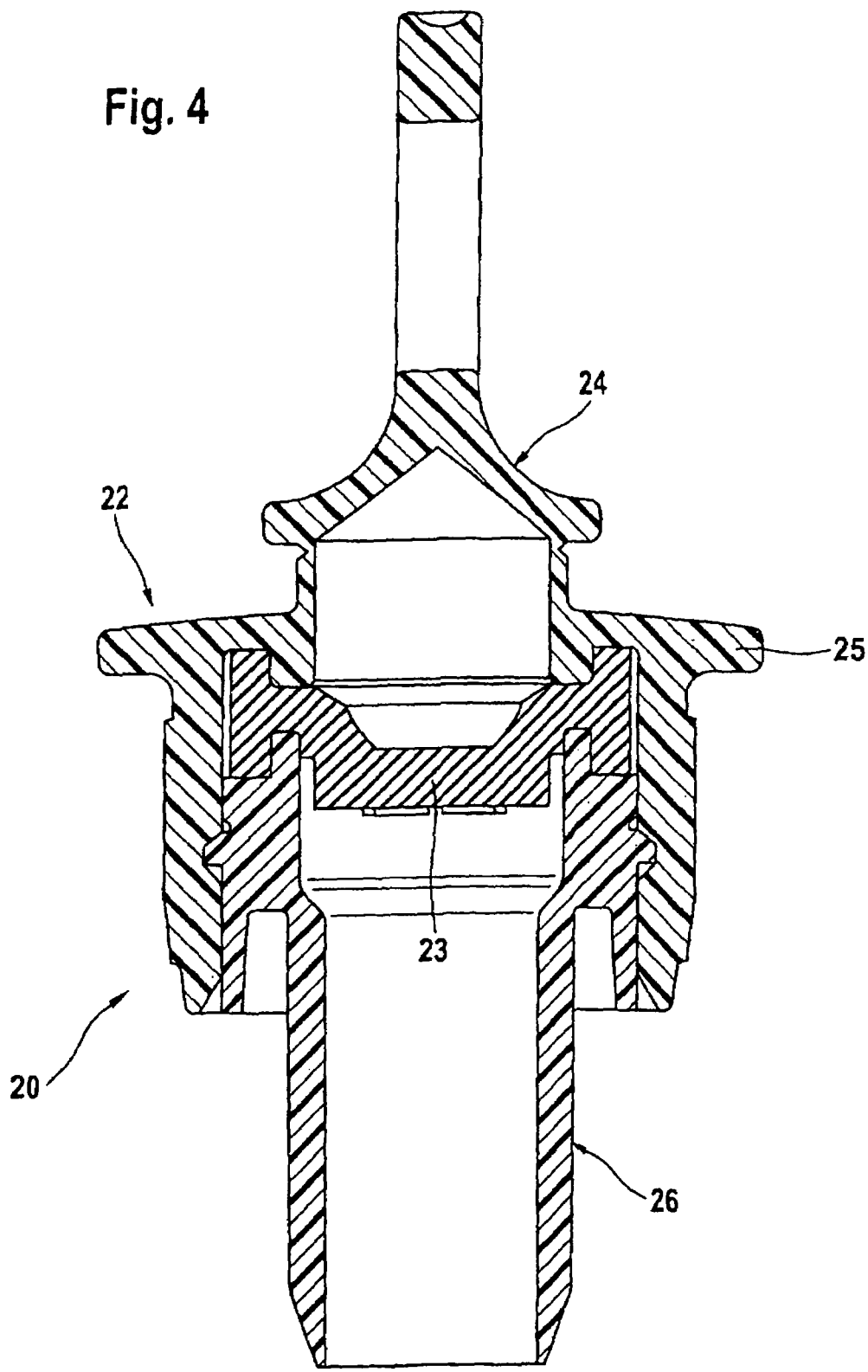
Figure 5:
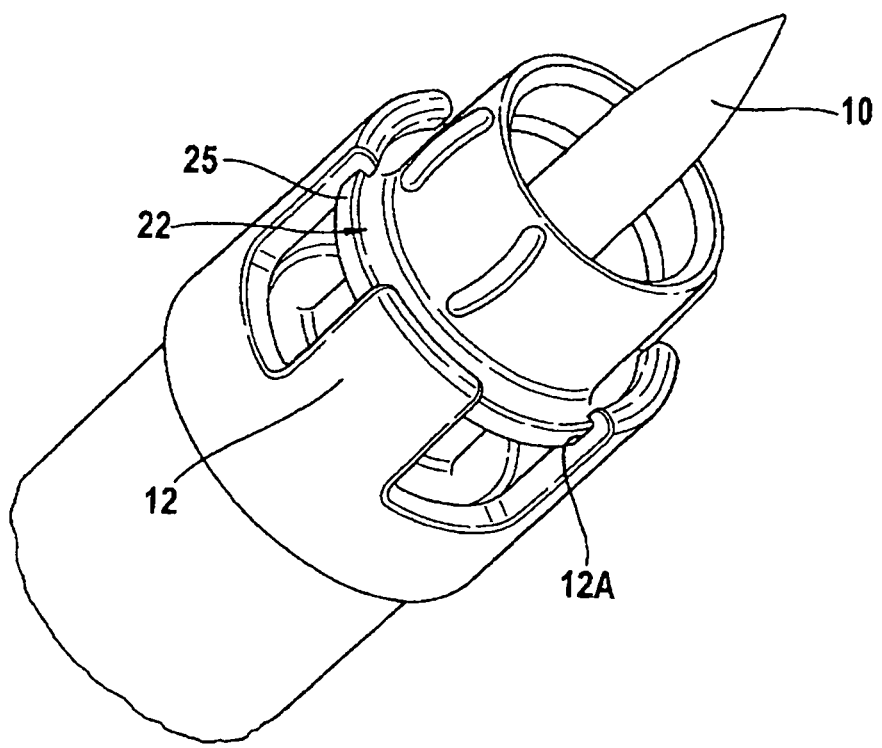

In the drawings:

FIG. 1 shows an infusion device with a drip chamber and infusion line according to the invention, FIG. 2 shows the drip chamber of the infusion device of FIG. 1 in a perspective view, FIG. 3 shows an infusion bag, to which the infusion device according to the invention can be connected, FIG. 4 shows a cross-section through the connector part of the infusion bag for the removal of fluid from the infusion bag of FIG. 3, in a magnified representation, FIG. 5 shows the connection of the drip chamber of the infusion device to the connector part of the infusion bag in a perspective representation.

FIG. 1 shows an infusion device according to the invention, which comprises the drip chamber according to the invention. Drip chamber 1 according to the invention is described in detail below.

Drip chamber 1 comprises an elongated housing body 2 made of transparent plastic, which surrounds a chamber 3. Housing body 2 has a distal inlet 4 and a proximal outlet 5. The drip chamber is disposed in such a way that, in the position of use, distal inlet 4 lies at the top and proximal outlet 5 at the bottom.

A connector part 6 for connecting the drip chamber to an infusion container is provided at distal inlet 4 of housing body 2. Connector part 6 is designed as a cap-shaped body, which is placed onto housing body 2 and is sealed with respect to the housing body. Connector part 6 can however also be a one-piece component of the housing body.

Connector part 6 of drip chamber 1 comprises a base part 7 sitting on housing body 2, which base part has a cylindrical section 8 which surrounds the upper edge of housing body 2, and has a central mounting piece 9 which surrounds a piercing spike 10. Piercing spike 10 comprises a fluid channel 10A, which extends into chamber 3 of housing body 2. Piercing spike 10 is preferably a one-piece component of mounting piece 9 of connector part 6. A ventilation channel, in which a sterile filter can be disposed, can also be provided for the ventilation of the system.

Connector part 6 of drip chamber 1 comprises a securing part 11 for the detachable securing of connector part 6 of drip chamber 1 to a connector part of an infusion container. Securing part 11 comprises a plurality of, e.g. four, securing elements 12 disposed along the circumference of a circle, said securing elements being formed on cylindrical section 7 of connector part 6 and extending upwards around piercing spike 10. Securing elements 12 form sections of a cylindrical body. Piercing spike 10 extends upwards beyond securing elements 12 (FIG. 2).

Securing elements 12 disposed at equal distances around the periphery of cylindrical section 7 are designed in such a way that they can easily be spread outwards away from piercing spike 10. For this purpose, it is sufficient for the securing elements to be made from a plastic which readily yields. The upper edge regions of securing elements 12 each comprise a groove 12A at the inner sides facing one another, said groove running along the circumference of a circle.

Apart from drip chamber 1, the infusion device according to the invention comprises an infusion line 13 which is connected to proximal outlet 5 of the drip chamber. Located at the proximal end of the hose line is a connection piece 14, for example a Luer-Lock connector, for the connection of a cannula. A conventional hose clamp 15 is provided on infusion line 13 in order to interrupt the infusion.

FIG. 3 shows infusion container 16, to which drip chamber 1 of the infusion device can be connected. Infusion container 16 is a conventional infusion bag, which comprises two film layers 17 which are welded together at upper and lower edge 18, 19 in the position of use. Welded into lower edge 19 of the infusion bag are two connector parts 20, 21, whereof one connector part 20 forms a removal part and other connector part 21 forms an injection part. Infusion bag 16 is filled with an infusion solution, for example with a cytostatic.

Film bag 16 with removal part and injection part 20, 21 is described in detail in DE 102 23 560 A1, to which reference is expressly made for the purpose of disclosure. FIG. 4 shows a cross-section through removal part 20 of film bag 16 in a magnified representation. Since removal part 20 is described in detail in DE 102 23 560 A1, only the components essential to the invention will be explained briefly below.

Connector part 20 of infusion bag 16 comprises a tubular section 26 on the bag side, said section being welded to the bag, and an essentially cylindrical section 22 on the connection side, between which a piercing part 23, for example a self-sealing membrane made of elastic material, is disposed. Section 22 of connector part 20 on the connection side is closed with a turn-off closure part 24. Section 22 of connector part 20 on the connection side represents a securing part for securing the drip chamber. For this purpose, section 22 on the connection side comprises a peripheral shoulder 25 which extends radially outwards. The cross-section of peripheral shoulder 25 corresponds to the shape of grooves 12A of securing elements 12.

Closure part 24 is turned off by connector part 20 in order to connect drip chamber 1 to infusion bag 16, so that piercing part 23 lies free. Drip chamber 1 is then placed onto securing part 22 of connector part 20, whereby piercing spike 10 first pierces piercing part 23 of connector part 20 of infusion bag 16 and then securing elements 12 are arched outwards slightly until peripheral shoulder 25 of connector part 20 is fixed firmly in a snap-in manner in grooves 12A of securing elements 12. Drip chamber 1 is thus securely held to infusion bag 16, without the risk of piercing spike 10 slipping out of piercing part 23 of connector part 20.

FIG. 5 shows, in a perspective view, connector part 6 of drip chamber 1 and section 22 of connector part 20 of infusion bag 16 on the connection side, self-sealing membrane 23 not being inserted into section 22 on the connection side. It can clearly be seen how securing elements 12 engage on all sides around section 22 of connector part 20 on the connection side.

The invention claimed is:

1. A drip chamber for an infusion device with
   an elongated housing body, which housing body surrounds a chamber and comprises a distal inlet and a proximal outlet, and
   a connector part, which is provided at the distal inlet of the housing body for connecting the drip chamber to a connector part of an infusion container, which comprises a piercing spike with a fluid channel which can be inserted into a piercing part of the connector part of the infusion container and which extends into the chamber of the housing body,
   wherein the connector part of the drip chamber comprises a securing part for the detachable securing of the connector part of the drip chamber to the connector part of the infusion container,
   the securing part of the drip chamber comprises a plurality of securing elements disposed along the circumference of a circle, said securing elements comprising grooves at inner sides facing one another, said grooves running along the circumference of a circle, wherein the securing elements are designed in such a way that the securing elements can be spread from a position firmly engaging around the securing part of the infusion container into a position releasing the securing part of the infusion device; and
   the piercing spike in a center of the securing elements projects beyond the securing elements.

2. The drip chamber according to claim 1, characterized in that the securing part of the drip chamber is constituted as a cap-shaped body which is placed onto the housing body of the drip chamber.

3. The drip chamber according to claim 2, characterized in that the connector part of the drip chamber comprises a cylindrical base part which is placed onto the housing body of the drip chamber and on which the securing elements are formed.

4. The drip chamber according to claim 3, characterized in that the base part of the connector part of the drip chamber comprises a central mounting piece which surrounds the piercing spike.

5. The drip chamber according to claim 4, characterized in that the piercing spike is a one-piece component of the mounting piece.

6. The drip chamber according to claim 5, characterized in that the connector part of the drip chamber is an injection-molded part.

7. An infusion device with a drip chamber according to claim 1 and an infusion line, which is to be connected to a patient and which is connected to the proximal outlet of the housing body of the drip chamber.

8. An arrangement comprising an infusion container for accommodating a medical fluid and an infusion device according to claim 7, characterized in that the infusion container comprises a connector part with a piercing part for the insertion of the piercing spike of the drip chamber and a securing part, wherein the securing part of the connector part of the infusion container comprises a peripheral shoulder which is constituted such that the peripheral shoulder can be secured in a snap-in manner in the grooves of the securing part of the drip chamber.

9. The arrangement according to claim 8, characterized in that the securing part of the infusion container is an essentially cylindrical section on which the peripheral shoulder is formed.

10. A drip chamber for an infusion device with
    an elongated housing body, which housing body surrounds a chamber and comprises a distal inlet and a proximal outlet, and
    a connector part, which is provided at the distal inlet of the housing body for connecting the drip chamber to a connector part of an infusion container, which comprises a piercing spike with a fluid channel which can be inserted into a piercing part of the connector part of the infusion container and which extends into the chamber of the housing body,
    wherein the connector part of the drip chamber comprises a securing part for the detachable securing of the connector part of the drip chamber to the connector part of the infusion container,
    the securing part of the drip chamber comprises a plurality of securing elements disposed along the circumference of a circle, said securing elements comprising undercuts at inner sides facing one another, said undercuts running along the circumference of a circle, wherein the securing elements are designed in such a way that the securing elements can be spread from a position for firmly engaging around the securing part of the infusion container into a position for releasing the securing part of the infusion device, the undercuts being configured such that the securing elements are permanently secured in the position firmly engaging around the securing part of the infusion container; and
    the piercing spike in a center of the securing elements projects beyond the securing elements.

11. An arrangement of an infusion container for accommodating a medical fluid and a connector, the connector being in fluid communication with a drip chamber comprising an elongated housing body surrounding a chamber and having a distal inlet being in fluid communication with the connector and a proximal outlet being in fluid communication with an infusion line which is to be connected to a patient, wherein
    the infusion container comprises a connector part with a piercing part and the connector comprises a piercing spike with a fluid channel which can be inserted into the piercing part of the connector part of the infusion container and which extends into the chamber of the housing body,
    the infusion container comprises a securing part and the connector comprises a securing part,
    the securing part of the connector comprises a plurality of securing elements disposed along the circumference of a circle, said securing elements comprising grooves at inner sides facing one another, said grooves running along the circumference of a circle,
    the securing elements are designed in such a way that the securing elements can be spread from a position firmly engaging around the securing part of the infusion container into a position releasing the securing part of the infusion container,
    the securing part of the infusion container comprises a peripheral shoulder which is constituted such that the peripheral shoulder can be secured in a snap-in manner in the grooves of the securing part of the connector, and the piercing spike in a center of the securing elements projects beyond the securing elements.

12. An arrangement of an infusion container for accommodating a medical fluid and a connector, the connector being in fluid communication with a drip chamber comprising an elongated housing body surrounding a chamber and having a distal inlet being in fluid communication with the connector and a proximal outlet being in fluid communication with an infusion line which is to be connected to a patient, wherein the infusion container comprises a connector part with a piercing part and the connector comprises a piercing spike with a fluid channel which can be inserted into the piercing part of the connector part of the infusion container and which extends into the chamber of the housing body, the infusion container comprises a securing part and the connector comprises a securing part, the securing part of the connector comprises a plurality of securing elements disposed along the circumference of a circle, said securing elements comprising undercuts at inner sides facing one another, said undercuts running along the circumference of a circle, the securing elements are designed in such a way that the securing elements can be spread from a position for firmly engaging around the securing part of the infusion container into a position for releasing the securing part of the infusion container, the undercuts being configured such that the securing elements are permanently secured in the position firmly engaging around the securing part of the infusion container, and the securing part of the infusion container comprises a peripheral shoulder which is constituted such that the peripheral shoulder can be secured in a snap-in manner in the undercuts of the securing part of the connector, and the piercing spike in a center of the securing elements projects beyond the securing elements.

* * * * *